United States Patent [19]

Angstadt

[11] 4,110,250
[45] Aug. 29, 1978

[54] AMMOXIDATION PROCESS AND CATALYST

[75] Inventor: Howard P. Angstadt, Media, Pa.

[73] Assignee: Suntech, Inc., Wayne, Pa.

[21] Appl. No.: 788,864

[22] Filed: Apr. 19, 1977

Related U.S. Application Data

[62] Division of Ser. No. 750,092, Dec. 13, 1976, Pat. No. 4,044,042.

[51] Int. Cl.$^2$ .................... B01J 21/02; B01J 27/02; B01J 23/16
[52] U.S. Cl. .................... 252/432; 252/439; 252/464
[58] Field of Search .................... 252/432, 464, 439

[56] References Cited

U.S. PATENT DOCUMENTS

| | | | |
|---|---|---|---|
| 3,959,337 | 5/1976 | Bushick et al. | 260/465 C |
| 3,987,078 | 10/1976 | Dickason | 252/432 X |
| 4,052,418 | 10/1977 | Suresh et al. | 252/432 X |

*Primary Examiner*—Delbert E. Gantz
*Assistant Examiner*—William G. Wright
*Attorney, Agent, or Firm*—J. Edward Hess; Donald R. Johnson; Paul Lipsitz

[57] ABSTRACT

An ammoxidation process for the preparation of nitriles by reaction of an alkyl substituted armoatic hydrocarbon with ammonia and oxygen using as catalyst an α-alumina supported vanadium-alkali metal bronze promoted with boron, titanium, and tellurium whereby various desirable reaction parameters are obtainable. The invention also embodies the promoted catalyst.

7 Claims, No Drawings

AMMOXIDATION PROCESS AND CATALYST

This is a divisional application of Ser. No. 750,092 filed Dec. 13, 1976 now U.S. Pat. No. 4,044,042.

Ammoxidation processes are well known in the art and numerous processes with and without added oxygen and with numerous catalysts are described in various U.S. and foreign patents and publications. In those processes using added oxygen, several serious problems have hindered commercial development. One of the major problems where a nitrile is desired is that the selectivity to nitrile products is low due to the burn of hydrocarbon which reduces yield of nitrile products. It is also necessary for a commercially viable ammoxidation process to obtain good conversion, a high yield of product, an efficient use of ammonia, and to operate at relatively low mole ratios of ammonia and oxygen to hydrocarbon. A process that can achieve a plurality of these requirements would represent a significant advance in the art.

The use of vanadium oxides as catalysts in ammoxidation processes is well known. Also mixtures of vanadium oxide and other materials such as oxides of chromium, arsenic, selenium, sulfur, and antimony have been used (see U.S. Pat. No. 3,544,617). Molybydenum oxide and heteropoly acids such as phosphomolybdic acid together with promoters of tellurium oxide are also known as ammoxidation catalysts (British Pat. No. 948,014). Tellurium and bismuth promoted cerium-molbydocyanadic acids have also been disclosed as ammoxidation catalysts (U.S. Pat. No. 3,452,077). British Pat. No. 957,022 discloses the use of solid phosphoric acid activated with numerous metals and non-metals, including titanium and boron, as catalysts for ammoxidation of propylene to acrylonitrile. Similarly, a mixture of vanadium pentoxide and tellurium oxide is suggested as an ammoxidation catalyst (Br. Pat. No. 1,133,216). More recently compounds known as vanadium bronzes have been disclosed as catalyst for ammoxidation (see Belgian Pat. No. 820,903 and niobium has been used as a promoter for such catalysts (U.S. Pat. No. 3,959,336).

It has now been found that an ammoxidation process which gives good nitrile yields at high conversion and many of the other above mentioned objectives is achieved by catalytically reacting an alkyl substituted aromatic hydrocarbon with ammonia and oxygen using as catalyst a vanadium-alkali metal bronze supported on $\alpha$-alumina and promoted with a specific combination of boron, titanium and tellurium. The invention also embodies the novel catalyst composition.

The process of the invention is carried out in either a fixed bed mode of operation or in a fluidized bed at a temperature between about 375° C and 500° C, preferably 400° C to 459° C, most preferably about 425° C to 435° C. The source of oxygen is preferably air, but any oxygen source is suitable. The amount of oxygen used in the process may vary over wide limits, but the process enables rather limited amounts of oxygen to be used and this, in turn, is favorable in that less burn of hydrocarbon reactant occurs. Thus, the ratio of oxygen to hydrocarbon in the reactant stream will usually be up to about 6:1, although it is preferable to use no more than about 3:1, preferably 2.5:1 to 3:1, although about 2.0:1 is also quite useful. Likewise the ratio of ammonia to hydrocarbon used in the process of the invention will be preferably about 3:1, or less, most preferably 2.0:1 to 3:1 although higher ratios, up to 6:1 are also useful. It is also to be understood that the volume percent concentration of reactants in the feed may be quite high as compared to most ammoxidation procedures and the feed may comprise in percent by volume 5 to 25% hydrocarbon, 6 to 20% oxygen, and 6 to 35% ammonia. In the preferred method, the volume percent concentration of reactants corresponding to the above preferred ratios will comprise in percent by volume from about 5 to about 7% p-xylene, from about 15 to about 20% oxygen, and from about 10 to about 20% ammonia. The fact that the process of this invention makes possible this high concentration of reactants is significant in contributing to a very efficient overall process.

As indicated, the hydrocarbon reactant will be an alkyl (preferably lower alkyl; e.g.; 1 to 4 carbon atoms such as methyl, ethyl, propyl and butyl) substituted aromatic hydrocarbon and will be preferably of the benzene and naphthalene series. Most preferably, a member of the benzene series will be used such as toluene and meta and para-xylene. When using m-xylene to obtain isophthalonitrile, however, it is preferred to employ temperatures at the lower end of the range given above and this is in accord with art knowledge that m-xylene is more sensitive to carbon oxide formation than is the p-isomer.

It will be understood that the contact time for the reactants over the catalyst will vary over a wide range, but will usually be from about 0.1 to 20 seconds. The contact time actually used will depend upon catalyst loading, catalyst volume, temperature and other parameters and the skilled art worker will have no difficulty in selecting an appropriate contact time dependent upon these reaction parameters.

The reactant feed stream will, of course, contain other materials, as for example, the inert ingredients of air, recycled intermediates (e.g., a mononitrile when a dinitrile is desired) and possibly some small amounts of other by-products associated with the recycle stream. This use of a recycle stream will make possible a still more efficient process.

In addition to the above required parameters of the process it is essential that a particular type of material be used as catalyst. It is known in the art that the addition of an alkali metal compound to vanadium pentoxide will, when the mixture is heated yield complex materials with anomalous valencies known as a vanadium bronze. Such lithium bronzes are discussed by Volkov et al., Zh. Neorg. Khim: 17 (6): 1529-1532 (1972). Vanadium bronzes with sodium are described by Pouchard et al., Bull de la Soc. Chimique de France, No. 7, pages 2742-45 (1968), and No. 11 pages 4343-4348 (1967). Similarly, potassium containing vanadium bronzes are discussed by Holtzberg et al., J. Am. Chem. Soc. Vol. 78, pages 1536-40 (1956). Lithium bronzes are described by Hardy et al., Bull de la Soc. Chimique de France, No. 4, 1056-65 (1965) and by Reisman et al., Jour Physical Chemistry 66 1181-85 (1962). Also of interest is the article by P. Hagenmuller entitled "Tungsten Bronzes, Comprehensive Inorganic Chemistry", edited by J. C. Bailar, Jr. et al and published in 1973 by Pergamon Press.

All of the above references as well as the references which follow are hereby incorporated herein to teach the chemistry and preparation of the bronzes which are used in this invention.

These bronze materials are prepared by mixing an appropriate alkali metal compound (e.g., carbonate, oxalate, etc.) with vanadium pentoxide and heating the mixture at an elevated temperature for several hours.

Depending upon the amount of alkali metal ion added certain phases will be established in accordance with the particular phase diagram pertinent to the mixture. Thus, for example, the Holtzbert et al. article referred to above describes the potassium bronze system and the sodium system is shown in the article by Slodbodin et al., J. Appl. Chem, (USSR) Vol. 38, pp. 799-803 (April 1965). Of the above alkali metal vanadium bronzes, all of which may be used in the process of the invention, the preferred bronzes for use as catalysts are the sodium bronzes and mixtures of the various species also may be employed. Preferred species include Bronze I (BZ I) which has an atomic ratio of sodium to vanadium of 0.167, Bronze II (BZ II) where the atomic ratio is 0.417, and an alpha prime phase ($\alpha'$-phase) where the atomic ratio is 0.50. The terms Bronze I and Bronze II are used herein because these compounds correspond to the compounds called "first BRONZE" and "second BRONZE" by Slobovin and Fotiey, Jour. Applied Chemistry (USSR) 38 Vol. 4 pg. 799 April 1965 where the first bronze is characterized by having 14.3 mole percent of $Na_2O$ in its composition (as does BZ I). These preferred BRONZE I and $\alpha'$-phase bronzes may be further characterized by the generic empirical formula $Na_xV_2O_5$ where $x$ is greater than zero and equal to or less than 1. Other bronze systems of the $Na_xV_2O_5$ species are known where x is greater than 1 and these are useful in the process, but are somewhat unstable and therefore not preferred. The BZ I species may be considered as $Na_2O \cdot V_2O_4 \cdot 5V_2O_5$ or $Na_{0.33}V_2O_5$ which is shown together with related members of the series at pages 573 to 575 of the Hagenmuller article as $\beta$-$Na_xV_2O_5$ where $x$ varies from 0.22 to 0.40, the "$\beta$" designation indicating the particular crystal phase structure of the compound. The BZ II species may be considered as $5NA_2O \cdot V_2O_4 \cdot 11V_2O_5$ or as $Na_{1+x}V_3O_8$ ($x=0.25$) which is isotypic with $Li_{1=x}V_3O_8$ and is shown at page 584 of the Hagenmuller article mentioned above. The $\alpha'$-phase is characterized as $Na_xV_2O_5$ where $x+ +0.7$ to 1.0 (see page 577 of the Hagenmuller article). Also characteristic of the bronzes are their x-ray diffraction patterns wherein the strongest lines are as follows:

BZ I: 9.6, 7.3, 4.75, 3.87, 3.47, 3.38, 3.21, 3.11, 3.08, 2.92, 2.90, 2.727, 2.55, 2.45, 2.38, 2.18, 1.97, 1.87, 2.803, 1.74, 1.535, 1.492.

BZ II: 6.9, 7.04, 5.81, 3.87, 3.62, 3.50, 3.45, 3.21, 3.10, 3.01, 3.67, 2.57, 2.43, 2.32, 2.27, 2.02, 1.97, 1.96, 1.81, 1.72, 1.86, 1.504, 1.333, 1.39.

$\alpha'$: 11.3, 5.645, 4.82, 4.436, 3.667, 3.456, 2.967, 2.889, 2.882, 2.799, 2.604, 2.436, 2.412, 2.291, 2.0196, 1,889, 1.803, 1.77, 1.689, 1.635, 1.592, 1.479.

The $\alpha$-prime phase as with the other bronzes may be obtained by the methods described in the literature and placed on the support for use in the process, or it may be made in situ. This is readily achieved by treating the BZ II on the support with a reducing atmosphere (e.g., ammonia) or a stream similar to the hydrocarbon, ammonia and oxygen; e.g., an oxygen to hydrocarbon mole ratio of less than about 3.0.

As indicated the catalyst bronzes may comprise a mixture of the above discussed bronzes and preferred catalysts will comprise a mixture predominant in either BZ II or the $\alpha$-prime phase or both. While BZ I used above is operable, it is preferred in order to keep the carbon oxides to a minimum to avoid having a predominant amount of BZ I in the catalyst composition.

In order to obtain the specific promoted catalyst used in the invention, the appropriate compounds are simply added during the catalyst preparation. In one technique the oxides of boron (e.g. $B_2O_3$), titanium (e.g. $TiO_2$) and tellurium (e.g. $TeO_2$) are added to all of the powdered catalyst ingredients (including the support) and physically mixed and the mixture pressed into pellets for use. In another technique water soluble salts (e.g., sodium borate, titanium oxalate, and sodium tellurite) are added and used with the other catalyst ingredients to impregnate the support. The amount of total promoter loading on the total catalyst and its support will be from about 4.1% to about 6.3% by weight calculated as the promoter oxides on the total finished catalyst (e.g. catalyst, promoters and support). However, the proportion of boron is very important since experimental data has shown that in order to achieve the advantages of the process the amount of boron promoter must be from about 0.15 to about 0.3 weight percent (as oxide) or the total catalyst and its support. The amount of titanium and tellurium will be on the order of about 2% to about 3% be weight (as oxides) of the total catalyst and support and although more may be used it is not usually economic to do so.

The catalyst support used in the process of the invention will be comprised of $\alpha$-alumina. $\alpha$-alumina is well known in the art and is exemplified by natural corundum and by the synthetic varieties which are commercially available. These materials have a high density (on the order of about 0.75 to 1.0 gm/cc) and very low surface area (on the order of $6m^2$/gm or less). Generally the $\alpha$-alumina will contain enough sodium ions so that the sodium bronzes may be made without any addition of sodium or other alkali metal compounds, but if insufficient sodium is present, enough may be added to give the desired bronze. In making the supported catalyst all that is required is to make an aqueous slurry of powdered (170 mesh or finer) $\alpha$-alumina, alkali metal salt (preferably carbonate) $V_2O_5$ and promoter compounds, evaporate off the water, pelletize and calcine the pellets at about 500° C–600° C for several hours, while passing a slow flow of air through the furnace. Alternatively the catalyst may be placed on the support by an impregnation technique where an aqueous vanadium oxalate solution containing the appropriate amount of alkali metal and promoter compounds are deposited onto the $\alpha$-alumina support.

As pointed out above, in making the catalyst alkali metal ions (usually in the form of the carbonate) are added to ensure that a bronze is formed. In a particularly preferred catalyst system where a sodium-vanadium bronze is desired, the amount of sodium ion employed to make the catalyst will be at a ratio of sodium to vanadium of 0.30 and such catalyst appears to be of high bronze purity devoid of extraneous materials which might degrade catalyst performance.

The amount of catalyst on the support (e.g., catalyst loading) will be from about 1 to 20% by weight, preferably about 3 to 8%. The surface area of the catalysts used in the process is generally quite low being less than $10m^2$/gm and usually 1 to $5m^2$/gm.

After the promoted BZ I or a promoted mixed BZ 1 and BZ II catalyst is prepared, but before its use, it is preferred to age the catalyst by a heat treatment at about 500° C to about 750° C for 3 to 4 hours. This treatment will convert most, if not all, of the BZ I to BZ II which is preferred over BZ I.

The catalyst composition of the invention is thus a supported alkali metal vanadium bronze promoted with from about 0.15 to about 0.3% by weight of $B_2O_3$, on the order of about 2% to about 3% of $TiO_2$ and about 2% to about 3% of $TeO_2$ and is preferably a promoted Bronze II or α-prime phase catalyst. The support for the catalyst, as pointed out above, is α-alumina and the supported catalyst is preferably pelletized for use, but may also be employed in powder form.

The ammoxidation is carried out preferably in conventional fixed or fluidized bed apparatus, the reaction gases passing over the catalyst at reaction temperature and the effluent gases separated into the appropriate product and recycle streams. Particular advantages of the process of the invention reside in (a) low formation of carbon oxides, (b) high selectivity for formation of nitriles, (c) low oxygen and ammonia to hydrocarbon ratios, (d) efficient use of ammonia, (e) reduced dealkylation of polyalkyl aromatics and (f) rather low process temperature. In order to further describe and illustrate the invention the following examples are given:

PREPARATION OF CATALYSTS

Method A

The α-alumina support is ground into a fine powder having a particle size of about 170 mesh or less and the appropriate amount of $B_2O_3$, $TiO_2$, $TeO_2$ and $V_2O_5$ added to it. If analysis shows that the amount of alkali metal in the α-alumina is insufficient the desired amount of sodium carbonate or other alkali metal salt is added. The mixture is ground dry and then water is added and the mixture further agitated to make a slurry. The slurry is poured into an evaporating dish and evaporated to dryness. The dry residue is mixed further to break up agglomerates and water added to make a paste which is formed into pellets and then calcined at 540° C for about 4 hours while air at the rate of 2.5 l/min is passed through the furnase. After cooling the catalyst pellets are ready for use.

Method B

Granulated alumina (8-16 mesh) is heated at 1300° C for 4 hours. Water soluble salts of the promoters and vanadium pentoxide are suspended in 5 parts of water, heated to 80° C, and oxalic acid is added slowly to obtain a blue-colored vanadium oxalate solution. Sodium carbonate, as needed, is added and the alumina is also placed in the solution. The mixture is dried over a water bath with agitation. While air is pumped in, it is indurated in a furnace at 400° C for 16 hours to obtain the catalyst which is ready for use after cooling.

EXPERIMENTAL PROCEDURES

An appropriate quantity of catalyst (with or without inert diluent, e.g, quartz) was placed in a fixed bed ¼ inch annular stainless steel reactor. Inert packing above the catalyst serves as a preheater section and a small amount (about 1-2 inches) of similar inert packing was placed in the bottom of the reactor to support the catalyst in the reaction zone. The upper end of the reactor was equipped with an assembly having multiple openings through which the hydrocarbons, ammonia, and air (or oxygen-helium or oxygen-nitrogen mixtures) can be metered. The reactants were fed into the reactor which was operated at 30 psig. The rate of gas flow was adjusted so as to produce the desired contact time at a given reaction temperature and pressure over a given volume of catalyst.

The effluent gases were passed from the reactor into a chilled flask where the products were collected along with ammonium carbonate and water. The remaining escaping gas was passed through a cold water cooled condenser, a water trap, an acid trap, a wet test meter, and finally captured in a large polyvinylchloride bag. The reaction products were extracted with acetonitrile and water, the solid products filtered off and the filtrate separated into solvent and water layers.

The analysis of the organic layer, water layer, gas sample from the bag, and the water trap, the acid trap, and the volume of the wet test meter enables calculation of the results (i.e., conversion, carbon balance, yield, etc.)

EXAMPLES I-IV

Using the above described procedure catalysts of a sodium-vanadium bronze on α-alumina containing 8% vanadium (as $V_2O_5$) and various amounts of promoters was prepared. Operating data for the ammoxidation process and the results obtained are shown in Table I.

TABLE I

Ammoxidaton of p-Xylene To Nitriles
Catalyst: Sodium-Vanadium Bronze (8% by wt.) on α-alumina promoted with boron, titanium, and tellurium.

| | Wt. % B/Ti/Te (As oxides) | Temp. Range ° C | % Conversion | Yield (Mole Percent) | | | | | | |
|---|---|---|---|---|---|---|---|---|---|---|
| | | | | Carbon oxides | TN* | TPN+ | Total Nitriles | Ratio TPN Nitriles | % $NH_3$ Burn[3] | % Plant Yield |
| | I Mole Ratio- $NH_3$: p-xylene=2.5; $O_2$:p-xylene=2.5 | | | | | | | Contact Time=4.8 sec. | | |
| a) | 2/2/2 | 401/406 | 2.5 | 12.7 | 80.0 | 3.8 | 83.8 | 0.045 | 27.2 | 70 |
| b) | .5/2/2 | 410/416 | 7.1 | 4.9 | 84.6 | 9.4 | 94.0 | 0.100 | 20.9 | 89 |
| c) | .2/2/2 | 400/445 | 42.4 | 5.1 | 63.9 | 30.9 | 94.8 | 0.326 | 18.6 | 91 |
| d) | .1/2/2 | 400/436 | 37.5 | 5.8 | 62.8 | 31.1 | 93.9 | 0.331 | 8.0 | 90 |
| e) | .2/0/2 | 410/426 | 20.2 | 5.1 | 78.6 | 15.8 | 94.4 | 0.168 | 16.0 | 90 |
| f) | .2/2/0 | 401/450 | 35.6 | 7.2 | 59.1 | 33.3 | 92.4 | 0.360 | 14.4 | 87 |
| | II Mole Ratio- $NH_3$-p-xylene=5; $O_2$:p-xylene=4 | | | | | | | Contact Time=7 sec. | | |
| a) | 2/2/2 | 420/430 | 9.0 | 11.5 | 72.6 | 13.8 | 86.4 | 0.160 | 34.4 | 76.5 |
| b) | .5/2/2 | 420/425 | 15.5 | 6.3 | 78.4 | 14.6 | 93.0 | 0.157 | 32.9 | 87.6 |
| c) | .2/2/2 | 400/426 | 60.9 | 8.1 | 42.2 | 49.1 | 91.3 | 0.538 | 19.9 | 87.8 |
| d) | .1/2/2 | 420/441 | 48.0 | 6.0 | 54.5 | 39.0 | 93.5 | 0.418 | 37.2 | 90.5 |
| e) | .2/0/2 | 420/442 | 35.8 | 5.9 | 69.6 | 24.2 | 93.8 | 0.258 | 30.8 | 89.5 |
| f) | .2/2/0 | 419/440 | 34.9 | 8.7 | 69.1 | 21.9 | 91.0 | 0.241 | 27.6 | 84.8 |
| | III Mole Ratio- $NH_3$:p-xylene=3; $O_2$-p-xylene=2.5 | | | | | | | Contact Time=14.5 sec. | | |
| a) | 2/2/2 | 420/426 | 14.1 | 10.7 | 73.4 | 12.9 | 86.3 | 0.150 | 57.7 | 76.3 |
| b) | .5/2/2 | 420/427 | 24.6 | 6.2 | 73.7 | 18.9 | 92.6 | 0.204 | 26.4 | 87.0 |
| c) | .2/2/2 | 418/435 | 56.1 | 5.7 | 56.0 | 37.8 | 93.8 | 0.403 | 18.2 | 90.4 |
| d) | .1/2/2 | 420/432 | 46.0 | 8.2 | 50.8 | 40.2 | 91.0 | 0.442 | 28.0 | 86.3 |
| e) | .2/0/2 | 420/435 | 46.0 | 6.4 | 61.2 | 31.5 | 92.7 | 0.340 | 29.9 | 88.2 |
| f) | .2/2/0 | 420/441 | 52.2 | 9.2 | 53.6 | 36.4 | 90.0 | 0.405 | 22.2 | 84.7 |

TABLE I-continued

Ammoxidaton of p-Xylene To Nitriles
Catalyst: Sodium-Vanadium Bronze (8% by wt.) on α-alumina promoted with boron, titanium, and tellurium.

| | Wt. % B/Ti/Te (As oxides) | Temp. Range °C | % Conversion | Yield (Mole Percent) | | | | Ratio TPN / Nitriles | % NH$_3$ Burn[3] | % Plant Yield |
|---|---|---|---|---|---|---|---|---|---|---|
| | | | | Carbon oxides | TN* | TPN+ | Total Nitriles | | | |
| | IV MOle Ratio- NH$_3$:p-xylene=3.0; O$_2$:p-xylene=2.5 | | | | | | | Contact Time=9 sec. | | |
| a) | 2/2/2 | 421/421 | 7.1 | 9.2 | 76.8 | 12.0 | 88.8 | 0.135 | 20.0 | 80.3 |
| b) | .5/2/2 | 420/428 | 15.2 | 5.5 | 77.4 | 15.8 | 93.2 | 0.170 | 26.5 | 88.1 |
| c) | .2/2/2 | 420/451 | 54.4 | 6.0 | 57.1 | 36.2 | 93.3 | 0.388 | 21.5 | 89.6 |
| d) | .1/2/2 | 420/450 | 45.0 | 10.1 | 47.3 | 41.6 | 88.9 | 0.468 | 27.8 | 83.7 |
| e) | .2/2/0 | 420/449 | 46.0 | 7.6 | 52.1 | 39.8 | 91.9 | 0.433 | 20.5 | 87.6 |

*TN=Tolunitrile
+TPN=Terephthonitrile

As can be seen from the above Table I a plurality of desirable reaction parameters are achieved in runs Ic, IIc, IIIc and IVc, where the process is operated under the defined conditions of the invention. It is to be understood that in the operation of high volume commercial processes such as the ammoxidation process of this invention, a cost benefit analysis determines the optimum parameters for use. Even small improvements become significant because of the large volumes involved. Thus, a trade-off of the various parameters must be made and even though one or more particular parameters may be less than optimum, the overall process is the most efficient from an economic standpoint. In the above data in the C-case with a plurality of favorable parameters represents the most economical process within its set.

EXAMPLE V

In a similar ammoxidation with m-xylene at 436° C using the catalyst of Ic the process gave a 37.6% conversion, carbon oxides formation in the amount of 15.49 mole %, total nitriles in the amount of 83 mole %, an ammonia burn of 6.2% and a plant yield of 77%.

The invention claimed is:

1. A catalyst consisting essentially of an alkali metal vanadium bronze supported on α-alumina and promoted with about 2 to about 3% of tellurium, about 2 to about 3% of titanium and about 0.15 to about 0.3% of boron, said percentages being by weight of the total catalyst and its support and wherein said promoters are in the form of their oxides.

2. The catalyst of claim 1 where the bronze is a sodium vanadium bronze.

3. The catalyst of claim 2 where the bronze is predominantly BZ II or the α-prime phase.

4. The catalyst of claim 3 where the bronze is predominantly BZ II.

5. The catalyst of claim 3 where the bronze is predominantly the α-prime phase.

6. The catalyst of claim 2 where the bronze is a mixture of BZ II and the α-prime phase.

7. A catalyst composition consisting essentially of an α-alumina support, from about 1 to 20% by weight of the total catalyst of an alkali metal vanadium bronze and from about 0.15 to about 0.3% by weight of B$_2$O$_3$, about 2 to about 3% of TiO$_2$, and about 2 to about 3% of TeO$_2$.

* * * * *